US009050122B2

(12) United States Patent
Bogdoll

(10) Patent No.: US 9,050,122 B2
(45) Date of Patent: Jun. 9, 2015

(54) PLIERS

(75) Inventor: Robert Bogdoll, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 222 days.

(21) Appl. No.: 13/554,640

(22) Filed: Jul. 20, 2012

(65) Prior Publication Data

US 2013/0096608 A1    Apr. 18, 2013

(30) Foreign Application Priority Data

Jul. 22, 2011  (DE) .................. 10 2011 052 091

(51) Int. Cl.
*A61B 17/28* (2006.01)
*A61B 19/00* (2006.01)

(52) U.S. Cl.
CPC ......... *A61B 17/2804* (2013.01); *A61B 17/2816* (2013.01); *A61B 19/34* (2013.01)

(58) Field of Classification Search
CPC .............. B25B 7/00; B25B 7/06; B25B 7/08; B25B 7/12; B26B 13/00; B26B 13/28; A61B 17/2804; A61B 17/2816; A61B 19/34
USPC ............ 81/416, 415, 381, 383, 350; 606/208
See application file for complete search history.

(56) References Cited

U.S. PATENT DOCUMENTS

| 2,441,552 | A | * | 5/1948 | Barnes | 81/416 |
| 2,507,710 | A | * | 5/1950 | Grosso | 81/418 |
| 3,101,812 | A | * | 8/1963 | Mercer, Sr. | 184/105.1 |
| 2007/0068006 | A1 | * | 3/2007 | Schlichting et al. | 30/254 |
| 2013/0074659 | A1 | * | 3/2013 | Chang | 81/60 |

* cited by examiner

*Primary Examiner* — Hadi Shakeri
(74) *Attorney, Agent, or Firm* — Bachman & LaPointe, P.C.

(57) ABSTRACT

Pliers, in particular for surgical purposes, comprises a first plier half and a second plier half, wherein the plier halves are connected to each other via at least one joint, and wherein at least one of the plier halves is provided with at least one rinsing channel.

5 Claims, 1 Drawing Sheet

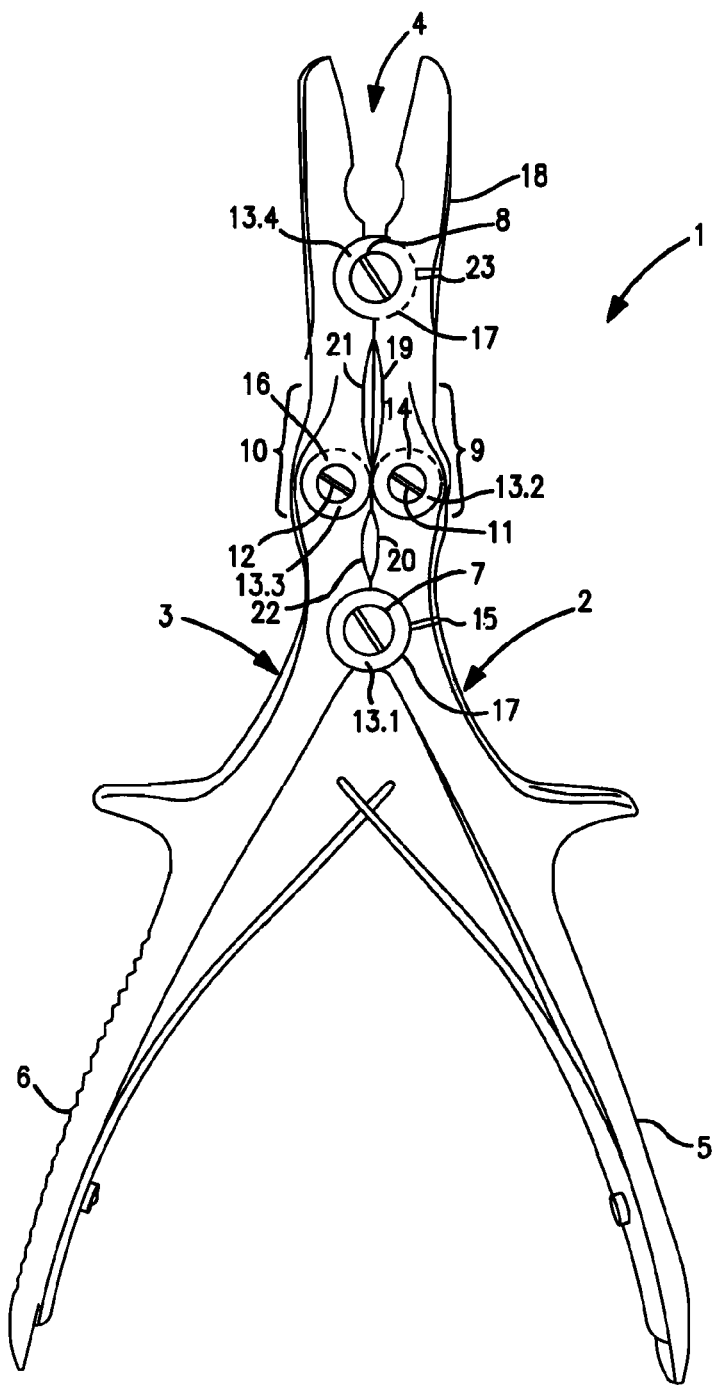

PLIERS

BACKGROUND OF THE INVENTION

The invention relates to pliers and, more particularly, pliers for surgical purposes.

The prior art discloses a multiplicity of pliers. The cleaning of said instruments is relatively complicated and repeatedly causes difficulties in practice.

It is the object of the invention to provide pliers which can be better cleaned and which can be produced cost-effectively, and to provide suitable cleaning apparatuses.

SUMMARY OF THE INVENTION

Pliers, in particular pliers for surgical purposes, preferably comprise a first plier half and a second plier half, wherein the plier halves are connected to each other via at least one joint, which may also be referred to as rollers. For simpler comprehension, the rollers are referred to below as joints. At least one of the plier halves expediently has at least one rinsing channel. This affords the advantage that the pliers can be better cleaned.

Pliers below mean all types of pliers, in particular for surgical purposes. By way of example, but not definitively, the pliers may be designed as simple pliers, geared pliers, a double roller instrument, gougers, nibblers or the like.

In typical exemplary embodiments, the rinsing channel has a diameter of 0.5 mm to 8 mm, preferably 1 mm to 3 mm, particularly preferably 1.5 mm. This affords the advantage of the rinsing channel being relatively small and of little dirt, if any at all, passing during the treatment through the rinsing channel into the treatment region. A further advantage of the small diameter of the rinsing channel is that the component is weakened as little as possible by a small opening.

The rinsing channel is preferably provided from the "outside" with an indentation. In this case, the "outside" means that side of the rinsing channel which is freely accessible without disassembly and/or operation of the pliers. The indentation particularly preferably has a diameter of approx. 2 mm. This affords the advantage of enabling cleaning devices to be easily positioned and/or fitted.

In typical exemplary embodiments, the rinsing channel is arranged in such a manner that it connects an outside or top surface of the plier half to an inner surface of a functional element of the joint. This affords the advantage of enabling the inner surfaces of the joint and of the functional elements of the joint to be better cleaned.

In typical exemplary embodiments, a joint preferably consists of a male functional element which engages in a female functional element. Even more preferably, the functional elements are connected by a screw.

In typical exemplary embodiments, the functional elements of the joint have a clearance with respect to one another. This affords the advantage of enabling rinsing liquid which is introduced through the rinsing channel and dirt washed out by the rinsing liquid to drain out better from the joint.

In typical exemplary embodiments, the rinsing channel is arranged in such a manner that it connects a female functional element of the joint to a top surface of the plier half. This affords the advantage of enabling the depression in the female functional element of the joint, in which dirt easily remains stuck, to be better cleaned.

In typical exemplary embodiments, the rinsing channel has a rinsing nozzle. The rinsing nozzle is preferably suitable for connection to a rinsing gun. The rinsing nozzle is preferably formed integrally with the rinsing channel. This affords the advantage of enabling a conventional rinsing gun to be fitted onto the rinsing nozzle of the rinsing channel in such a manner that rinsing is possible.

In typical exemplary embodiments, the rinsing channel is suitable for receiving a rinsing nozzle. For this purpose, a suitable rinsing nozzle is expediently inserted into the rinsing channel. This affords the advantage that the rinsing is possible in a very simple manner.

In typical exemplary embodiments, the rinsing channel comprises a thread suitable for receiving a rinsing nozzle. The rinsing nozzle preferably has a corresponding external thread for screwing into the thread of the rinsing channel. This affords the advantage of enabling a good connection to be produced between the rinsing nozzle and rinsing channel.

In typical exemplary embodiments, at least one of the plier halves has a recess. The recess is preferably arranged between a mouth part and a branch of the pliers.

The recess is particularly preferably arranged on an inside of the plier half such that, in an unloaded state of the pliers, the plier halves are at least partially spaced apart from each other between the mouth part and the branch. This affords the advantage that, during rinsing of the pliers in the rinsing machine, better cleaning is possible, since the surfaces which are spaced apart from one another can be cleaned. A further advantage is that, in the case of pliers having the rinsing channels already described, the rinsing liquid and dirt which is rinsed out of the joint during the rinsing of the rinsing channel can drain away even better.

In typical embodiments, the recesses are oval, round and/or are provided with a radius. The advantage afforded by the fact that there are no sharp edges is that no increased notch stress, which may result in fractures, occurs.

In typical exemplary embodiments, the recesses are provided symmetrically opposite one another in both plier halves. This affords the advantage that both plier halves are even further spaced apart from one another. It is also advantageous that the plier halves are of similar design and thus have the same properties, for example in respect of weight and stability.

In typical exemplary embodiments, the pliers comprise a plurality of joints. This affords the advantage that the pliers are geared pliers. In the case of pliers having a plurality of joints, at least one recess is preferably provided on an intermediate piece which connects the joints. This affords the advantage that, in the unloaded state, the relatively long intermediate pieces are spaced apart from one another and, as a result, can be better cleaned in cleaning apparatuses or rinsing machines.

Protection is claimed separately for a rinsing gun for rinsing a rinsing channel of pliers according to the described features. The rinsing gun is preferably designed in such a manner that it can be brought into operative connection with the rinsing channel in the pliers such that rinsing liquid can be introduced into the rinsing channel from the rinsing gun.

Protection is separately claimed for an attachment for a rinsing gun for rinsing a rinsing channel of pliers having the described features. The attachment is preferably suitable for engaging in the rinsing channel. The attachment preferably has an adapter suitable for connection to conventional rinsing guns. This affords the advantage that the pliers according to the invention can be cleaned in a simple manner using conventional rinsing guns.

BRIEF DESCRIPTION OF THE DRAWING

The invention is described briefly below with reference to the attached FIGURE which shows a schematic illustration of a top view of surgical geared pliers.

DETAILED DESCRIPTION

The FIGURE shows pliers 1, in particular for surgical purposes. The pliers 1 comprise a first plier half 2 and a second plier half 3. The two plier halves 2 and 3 form a plier mouth 4. Each of the plier halves 2 and 3 has a branch 5 and 6.

The pliers 1 are what are referred to as geared pliers. The pliers 1 therefore have a first joint 7 and a second joint 8.

A further term for joints is roller. Said terms are used synonymously below.

The joints 7 and 8 are respectively connected via an intermediate piece 9 and an intermediate piece 10 of the first plier half 2 and second plier half 3. Each of the intermediate pieces 9 and 10 comprises a buckling joint 11 and 12, respectively.

All of the joints 7 to 12 or rollers have a female joint element 13.1 to 13.4. A male joint element (not illustrated) which is arranged in the second plier half 3 or on the other side of the intermediate piece 9 or 10 engages in each case in said female joint element 13.1 to 13.4.

The pliers 1 comprise four rinsing channels 14, 15, 16 and 23.

The arrangement of the rinsing channel 23 at the second joint 8, by way of example, is described by way of example below. The rinsing channels 14, 15 and 16 are arranged analogously at the corresponding joints.

The rinsing channel 23 is arranged at the joint 8 in such a manner that an inner surface 17 (illustrated by dashed lines) of the female element 13.4 is connected to a top surface 18 of the pliers 1.

In an exemplary embodiment which is not shown, another rinsing channel may be arranged at another joint in such a manner that another inner surface of the male functional element can be connected to another top surface of the pliers.

Furthermore, the intermediate pieces 9 and 10 respectively have, in each case on the inner sides thereof facing each other, two recesses 19 and 20 and 21 and 22. The recess 19 is provided on the first plier half 2 between the joint 8 and the buckling joint 11. The second recess 20 is provided on the first plier half 2 between the joints 7 and the buckling joint 11. The recess 21 is provided analogously on the second plier half 3 between the joint 8 and the buckling joint 12. The recess 22 is provided on the second plier half 3 between the buckling joint 12 and the joint 7.

The present invention operates as follows:

After use, the pliers 1 can be cleaned by fitting a suitable rinsing gun onto one of the rinsing channels 14, 15, 16 or 23, or by means of a suitable attachment. Rinsing liquid penetrates the corresponding joint and between the plier halves 2 and 3 and cleans the intermediate space or the surfaces between the female and male joint elements.

The recesses 21 and 19 and 22 and 20 are provided in such a manner that, when the pliers 1 are not subjected to a load, the intermediate pieces 9 and 10 are at least partially spaced apart from each other. As a result, rinsing liquid introduced through the rinsing channels can particularly readily emerge in said region.

A further advantage is that the pliers 1 can be better cleaned in a rinsing machine, since the inner surfaces on the recesses 19 and 21 and 22 and 20 do not touch.

The invention claimed is:

1. A surgical pliers comprising:
a first pliers half; and
a second pliers half, the pliers halves are connected to one another via at least one joint;
at least one of the pliers halves has at least one rinsing channel;
the rinsing channel comprises a tubular channel having an inlet arranged in such a manner that it connects an upper surface of the at least one pliers half to an outlet at an inner surface of a functional element of the joint; and
the inlet of the rinsing channel is adapted to be fitted with a rinsing gun wherein rinsing liquid penetrates the joint.

2. Pliers according to claim 1, wherein the joint is formed by functional elements and the functional elements of the joint have clearance in relation to one another.

3. Pliers according to claim 1, wherein the rinsing channel is arranged in such a manner that it connects a female functional element of the joint to an upper surface of the pliers half.

4. Pliers according to claim 1, wherein at least one of the pliers halves has a mouth part and a branch, at least one recess, so that the pliers halves are in an unloaded state of the pliers at least partially spaced apart from one another between the mouth part and the branches.

5. Pliers according to claim 1, wherein the pliers have a plurality of joints, wherein at least one recess is provided on an intermediate piece connecting the joints.

* * * * *